United States Patent
Marcelpoil et al.

(10) Patent No.: US 7,065,236 B2
(45) Date of Patent: Jun. 20, 2006

(54) METHOD FOR QUANTITATIVE VIDEO-MICROSCOPY AND ASSOCIATED SYSTEM AND COMPUTER SOFTWARE PROGRAM PRODUCT

(75) Inventors: Raphaël Marcelpoil, Grenoble (FR); Thomas Gahm, Burlington, NC (US)

(73) Assignee: TriPath Imaging, Inc., Burlington, NC (US)

(*) Notice: Subject to any disclaimer, the term of this patent is extended or adjusted under 35 U.S.C. 154(b) by 756 days.

(21) Appl. No.: 09/957,446

(22) Filed: Sep. 19, 2001

(65) Prior Publication Data

US 2003/0091221 A1    May 15, 2003

(51) Int. Cl.
*G06K 9/00* (2006.01)
(52) U.S. Cl. ...................................................... 382/133
(58) Field of Classification Search ................ 382/128, 382/133; 356/406, 39
See application file for complete search history.

(56) References Cited

U.S. PATENT DOCUMENTS

| | | | |
|---|---|---|---|
| 4,191,940 A | 3/1980 | Polcyn et al. | |
| 4,887,892 A | 12/1989 | Bacus | |
| 4,997,769 A * | 3/1991 | Lundsgaard | ................. 436/66 |
| 4,998,284 A | 3/1991 | Bacus et al. | |
| 5,008,185 A | 4/1991 | Bacus | |
| 5,016,173 A | 5/1991 | Kenet et al. | |
| 5,109,429 A | 4/1992 | Bacus et al. | |
| 5,134,662 A | 7/1992 | Bacus et al. | |
| 5,202,931 A | 4/1993 | Bacus | |
| 5,432,865 A | 7/1995 | Kasdan et al. | |
| 5,625,705 A | 4/1997 | Recht | |
| 5,717,518 A | 2/1998 | Shafer et al. | |
| 5,732,150 A | 3/1998 | Zhou et al. | |
| 5,734,498 A * | 3/1998 | Krasieva et al. | ............ 359/387 |
| 5,784,162 A | 7/1998 | Cabib et al. | |
| 5,835,617 A * | 11/1998 | Ohta et al. | .................. 382/131 |
| 6,007,996 A | 12/1999 | McNamara et al. | |
| 6,031,930 A | 2/2000 | Bacus et al. | |
| 6,151,405 A | 11/2000 | Douglass et al. | |
| 6,453,060 B1 | 9/2002 | Riley et al. | |
| 6,577,754 B1 | 6/2003 | Stone et al. | |
| 6,819,787 B1 * | 11/2004 | Stone et al. | ................. 382/133 |

FOREIGN PATENT DOCUMENTS

| | | |
|---|---|---|
| EP | 1 065 496 A2 | 1/2001 |
| WO | WO 98/55026 A1 | 12/1998 |
| WO | WO 01/46657 A1 | 6/2001 |

* cited by examiner

*Primary Examiner*—Jingge Wu
*Assistant Examiner*—Ashutosh Upreti
(74) *Attorney, Agent, or Firm*—Alston & Bird LLP (57) ABSTRACT

A method of determining an amount of at least one molecular specie comprising a sample is provided, each molecular specie being indicated by a dye. The amount of the molecular specie is determined from an image of the sample captured as image data by a color image acquisition device in a video-microscopy system. An optical density of the sample is first determined in each of a red, green, and blue channel at a particular pixel in the image. A corresponding optical density matrix is thereafter formed for that pixel. The optical density matrix is then multiplied by the inverse of a relative absorption coefficient matrix so as to form a resultant matrix for the pixel. The relative absorption coefficient matrix comprises a relative absorption coefficient for each dye, independently of the sample, in each of the red, green, and blue channels. The resultant matrix thus comprises the amount of each molecular specie, as indicated by the respective dye, for that pixel. Associated systems and computer software program products are also provided.

87 Claims, 2 Drawing Sheets

METHOD FOR QUANTITATIVE VIDEO-MICROSCOPY AND ASSOCIATED SYSTEM AND COMPUTER SOFTWARE PROGRAM PRODUCT

FIELD OF THE INVENTION

The present invention relates to image analysis and, more particularly, to a method for quantitative video-microscopy in cellular biology and pathology applications and an associated system and computer software program product therefor.

BACKGROUND OF THE INVENTION

Effective analysis of microscopic images is essential in cellular biology and pathology, particularly for detection and quantification of genetic materials such as, for example, genes or messenger RNA, or the expression of this genetic information in the form of proteins such as through, for example, gene amplification, gene deletion, gene mutation, messenger RNA molecule quantification, or protein expression analyses. Gene amplification is the presence of too many copies of the same gene in one cell, wherein a cell usually contains two copies, otherwise known as alleles, of the same gene. Gene deletion indicates that less than two copies of a gene can be found in a cell. Gene mutation indicates the presence of incomplete or non-functional genes. Messenger RNAs (mRNA) are molecules of genetic information, synthesized from a gene reading process, that serve as templates for protein synthesis. Protein expression is the production of a given protein by a cell. If the gene coding for the given protein, determined from a protein expression process, is enhanced or excess copies of the gene or mRNA are present, the protein may be over-expressed. Conversely, if the gene coding is suppressed or absent, the protein may be under-expressed or absent.

Normal cellular behaviors are precisely controlled by molecular mechanisms involving a large number of proteins, mRNAs, and genes. Gene amplification, gene deletion, and gene mutation are known to have a prominent role in abnormal cellular behaviors through abnormal protein expression. The range of cellular behaviors of concern includes behaviors as diverse as, for example, proliferation or differentiation regulation. Therefore, effective detection and quantification in gene amplification, deletion and mutation, mRNA quantification, or protein expression analyses is necessary in order to facilitate useful research, diagnostic and prognostic tools.

There are numerous laboratory techniques directed to detection and quantification in gene amplification, deletion and mutation, mRNA quantification, or protein expression analyses. For example, such techniques include Western, Northern and Southern blots, polymerase chain reaction ("PCR"), enzyme-linked immunoseparation assay ("ELISA"), and comparative genomic hybridization ("CGH") techniques. However, microscopy is routinely utilized because it is an informative technique, allowing rapid investigations at the cellular and sub-cellular levels while capable of being expeditiously implemented at a relatively low cost.

When microscopy is the chosen laboratory technique, the biological samples must first undergo specific detection and revelation preparations. Once the samples are prepared, a human expert typically analyzes the samples with a microscope alone in a qualitative study, or with a microscope coupled to a camera and a computer in a quantitative and generally standardized study. In some instances, the microscope may be configured for fully automatic analysis, wherein the microscope is automated with a motorized stage and focus, motorized objective changers, automatic light intensity controls and the like.

The preparation of the samples for detection may involve different types of preparation techniques that are suited to microscopic imaging analysis, such as, for example, hybridization-based and immunolabeling-based preparation techniques. Such detection techniques may be coupled with appropriate revelation techniques, such as, for example, fluorescence-based and visible color reaction-based techniques.

In Situ Hybridization ("ISH") and Fluorescent In Situ Hybridization ("FISH") are detection and revelation techniques used, for example, for detection and quantification in genetic information amplification and mutation analyses. Both ISH and FISH can be applied to histological or cytological samples. These techniques use specific complementary probes for recognizing corresponding precise sequences. Depending on the technique used, the specific probe may include a chemical (ISH) marker or a fluorescent (FISH) marker, wherein the samples are then analyzed using a transmission microscope or a fluorescence microscope, respectively. The use of a chemical marker or a fluorescent marker depends on the goal of the user, each type of marker having corresponding advantages over the other in particular instances.

In protein expression analyses, immunohistochemistry ("IHC") and immunocytochemistry ("ICC") techniques, for example, may be used. IHC is the application of immunochemistry to tissue sections, whereas ICC is the application of immunochemistry to cultured cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

In both hybridization and immunolabeling studies, chromogens of different colors are used to distinguish among the different markers. However, the maximum number of markers that may be used in a study is restricted by several factors. For example, the spectral overlapping of the colors used to reveal the respective markers may be a limiting factor because dyes may absorb throughout a large portion of the visible spectrum. Accordingly, the higher the number of dyes involved in a study, the higher the risk of spectral overlapping. Further, the spectral resolution of the acquisition device may be a limiting factor and the minimal color shift that the device is able to detect must be considered.

In addition, immunochemistry, as well as chemistry in ISH, are generally considered to exhibit poor sensitivity when quantification of a marker must be achieved. However, the quantification accuracy of these techniques may be dependent upon several factors. For instance, the type of reaction used may play a role in the accuracy of the technique since the linearity of the relationship between ligand concentration and the degree of the immunochemical staining reaction may strongly depend on the reaction type.

More particularly, for example, a peroxidase/anti-peroxidase method may be more linear than a biotin-avidin method. The cellular localization of the markers may also affect accuracy where, for example, if membrane and nuclear markers spatially overlap, the resulting color is a mixture of the respective colors. Accordingly, since the corresponding quantification is subjective, the accuracy of the determination may be affected. In addition, a calibration standard such as, for example, cells with known features, gels with given concentrations of the marker, or the like, may be required where a developed analysis model is applied to a new and different case. Staining kits are generally available which incorporate calibration standards. However, the calibration standard is usually only applicable to a particular specimen, such as a specific cell or a structure of a specific type which is known to exhibit constant features with respect to the standard, and may be of limited utility when applied to a sample of a different nature.

Overall, the described "calorimetric" studies present sample analysis information in color and facilitate processing and quantification of the information to thereby help to provide a diagnosis or to form a prognosis of the particular case. For illustration, the detection and quantification of the HER2 protein expression and/or gene amplification may be assessed by different approaches used in quantitative microscopy. HER2 is a membrane protein that has been shown to have a diagnostic and prognostic significance in metastatic breast cancer. Because HER2 positive patients were shown to be more sensitive to treatments including Herceptin® (a target treatment developed by Genentech), the definition of the HER2 status of metastatic breast cancers has been proven to be of first importance in the choice of the appropriate treatment protocol. This definition of the HER2 status was based on a study of samples treated with either hybridization (FISH, ISH) or immunolabeling (IHC) techniques.

In such studies, using FISH with, for example, an FDA approved kit such as PathVysion® produced by Vysis, requires an image analysis protocol for counting the number of copies of the HER2 gene present in every cell. In a normal case, two copies of the gene are found in each cell, whereas more than three copies of the gene in a cell indicate that the gene is amplified. Alternatively, using IHC with, for example, an FDA approved kit such as Herceptest® produced by Dako, requires an image analysis protocol that classified the cases into four categories depending on the intensity and localization of the HER2 specific membrane staining. Current studies tend to show that these two investigation techniques (hybridization and immunolabeling) may be complementary and may help pathologists in tumor sub-type diagnosis when combined.

However, such colorimetry studies require extensive sample preparation and procedure control. Thus, when disposing of adapted staining protocols, it is critical to be able to verify that the staining for each sample matches the particular model used in the image acquisition and processing device such that useful and accurate results are obtained from the gathered information. Otherwise, the analysis may have to be repeated, starting again from the sample preparation stage, thereby possibly resulting in a costly and time-consuming process.

In a typical microscopy device based on image acquisition and processing, the magnified image of the sample must first be captured and digitized with a camera. Generally, charge coupled device (CCD) digital cameras are used in either light or fluorescence quantitative microscopy. Excluding spectrophotometers, two different techniques are generally used to perform such colorimetric microscopy studies. In one technique, a black and white (BW) CCD camera may be used. In such an instance, a gray level image of the sample is obtained, corresponding to a monochromatic light having a wavelength specific to the staining of the sample to be analyzed. The specific wavelength of light is obtained either by filtering a white source light via a specific narrow bandwidth filter, or by directly controlling the wavelength of the light source, using either manual or electronic controls. Accordingly, using this technique, the analysis time increases as the number of colors increases because a light source or a filter must be selected for every different sample staining or every different wavelength. Therefore, many different images of the sample, showing the spectral response of the sample at different wavelengths, must be individually captured in a sequential order to facilitate the analysis. When multiple scenes or fields of view must be analyzed, the typical protocol is to automate the sequence in a batch mode to conserve processing time.

According to a second technique, a color CCD digital camera is used, wherein three gray level images of the sample are simultaneously captured and obtained. Each gray level image corresponds to the respective Red, Green and Blue channel (RGB) of the color CCD camera. The images are then analyzed directly in the RGB color space by restricting the analysis to pixels located in a specific region of the RGB cube, the specific region also including pixels from a corresponding training database. Alternatively, the images are analyzed, after mathematical transform of the RGB color space, in one of the many color spaces defined by the CIE (International Commission on Illumination) such as, for example, an HLS (Hue, Luminance or Saturation) space. Alternatively, some camera manufacturers produce specific CCD cameras, wherein narrow bandwidth filters for targeting specific wavelengths may replace the usual Red, Green and Blue filters. In such an instance, the camera allows a fast image capture of the three spectral components of a scene in a parallel manner. However, cameras modified in this manner may be restricted to specific spectral analysis parameters because the filters cannot be changed and therefore cannot be adapted to address a unique dye combination used for the sample. Thus, the second technique generally relies upon either the detection of contrast between the specie/species of interest and the remainder of the sample or the analysis of the sample over a narrow bandwidth.

Accordingly, techniques used in calorimetric analyses of prepared samples are of limited use in the detection and quantification of species of interest due to several factors such as, for example, spectral overlapping, mixing of colors due to spatially overlap of membrane, cytoplasmic, and nuclear markers, chromatic aberrations in the optical path, limited spectral resolution of the acquisition device, calibration particularities, subjectivity of the detection and quantification process, and inconsistencies between human operators. The image processing portion of colorimetric analysis techniques has historically been directed to the subjective detection of contrast within the prepared sample or to a complex and voluminous analysis of the sample at various specific wavelengths of light using a combination of light sources and filters. Therefore, there exists a need for a simpler and more effective calorimetric analysis technique that overcomes detection and quantification limitations found in prior art analysis techniques. Such a technique should also be capable of providing high quality data, comprising the necessary analysis information about the sample, while reducing subjectivity and inconsistency in the sample analysis.

SUMMARY OF THE INVENTION

The above and other needs are met by the present invention which, in one embodiment, provides a method of determining an amount of at least one molecular specie comprising a sample, each molecular specie being indicated by a dye. The amount of the molecular specie is determined from an image of the sample captured as image data by a color image acquisition device in a video-microscopy system. First, an optical density of the sample is determined in each of a red, green, and blue channel at a particular pixel in the image. A corresponding optical density matrix is thereafter formed for that pixel. The optical density matrix is then multiplied by the inverse of a relative absorption coefficient matrix so as to form a resultant matrix for the pixel. The relative absorption coefficient matrix comprises a relative absorption coefficient for each dye, independently of the sample, in each of the red, green, and blue channels. The resultant matrix thus comprises the amount of each molecular specie, as indicated by the respective dye, for that pixel.

The amount of each molecular specie is determined from a color image of the sample. According to one embodiment of the present invention, a color image acquisition device, such as an RGB camera and associated frame grabber or a color scanner, is used to acquire the image of the sample. The image may then be balanced and normalized according to an empty field (white) reference and a black field image and, in some instances, corrected for shading. The image also corrected for chromatic aberrations on a channel by channel basis. Subsequently, an optical density of the sample is determined in each of the red, green, and blue channels at a particular pixel in the image from the measured transmitted light. A corresponding optical density matrix is thereafter formed for that pixel and then multiplied by the inverse of a relative absorption coefficient matrix of the dyes present in the sample so as to form a resultant matrix for the pixel representing the optical density contributions from each dye. Since the relative absorption coefficient matrix comprises a relative absorption coefficient for each of the dyes used in the sample preparation protocol in each of the red, green, and blue channels, the resultant matrix thus comprises the amount, as expressed in proportion to concentration, of each molecular species as indicated by the respective dyes for that pixel.

Another advantageous aspect of the present invention comprises a video-microscopy system for determining an amount of a molecular specie comprising a sample from an image of the sample, wherein each molecular specie is indicated by a dye. The system comprises a color image acquisition device capable of capturing a magnified digital image of the sample as image data, and a computer device operably engaged with the image acquisition device. The computer device comprises a processing portion configured to determine an optical density of the sample from the image data in each of a red, green, and blue channel and at a pixel in the image to thereby form a corresponding optical density matrix for the pixel. Another processing portion of the computer device is further configured to multiply the optical density matrix by the inverse of a relative absorption coefficient matrix so as to form a resultant matrix for the pixel of the image. The relative absorption coefficient matrix comprises a relative absorption coefficient for each dye, independently of the sample, in each of the red, green, and blue channels. The resultant matrix thus comprises the amount of each molecular specie, as indicated by the respective dye, for that pixel.

Still another advantageous aspect of the present invention comprises a computer software program product configured to be executable on a computer device and capable of determining an amount of a molecular specie comprising a sample from a digital image of the sample captured as image data by a color image acquisition device in a video-microscopy system, wherein each molecular specie is indicated by a dye. One executable portion of the computer software program product is capable of determining an optical density of the sample in each of a red, green, and blue channel and at a pixel in the image to thereby form a corresponding optical density matrix for the pixel. Another executable portion of the computer software program product is further capable of multiplying the optical density matrix by the inverse of a relative absorption coefficient matrix so as to form a resultant matrix for the pixel of the image. The relative absorption coefficient matrix comprises a relative absorption coefficient for each dye, independently of the sample, in each of the red, green, and blue channels. The resultant matrix thus comprises the amount of each molecular specie, as indicated by the respective dye, for that pixel.

Such imaging techniques as described herein, otherwise known as multi-spectral imaging techniques, when particularly adapted to color imaging, allow a substantially real time, or video rate, processing and viewing of the sample. The use of, for example, a RGB color CCD camera allows acquisition and processing time for sample images to be performed at a video rate, typically 40 millisecond per frame, which provides a considerable advantage as compared to prior art imaging techniques which generally exhibit field of view acquisition and processing times of over 1 second. Where an RGB camera is used by the system, image acquisition through the different channels is performed in parallel and look-up tables (LUT) can be generated so as to map the possible RGB color input values to predetermined concentrations and/or transmittance of each of various dyes. Thus, such capabilities may, for example, enhance processing speed and facilitate real time processing for display purposes.

Accordingly, an a posteriori evaluation of the image can be performed to evaluate the efficiency of an a priori known dye combination used to solve the linear equations for each pixel. That is, an evaluation as detailed herein also provides a confidence evaluation for each pixel in that the color and intensity measured at the given pixel may be justified by a combination of the a priori known dyes. Such a confidence evaluation can be expressed as the inverse to the closest match in the theoretical model. In a situation in which there are fewer dyes to evaluate than input channels (less unknown parameters than equations, e.g. one counter stain+ one marker (=2 dyes) when 3 input channels (RGB) are available), the redundant information may be used to minimize potential errors and therefore to maximize the accuracy of the detection and quantification system.

Thus, embodiments of the present invention comprise a calorimetric analysis technique for prepared samples that provides effective detection and quantification of species of interest that overcomes limiting factors of prior art techniques such as, for example, spectral overlapping, mixing of colors due to spatially overlap of membrane and nuclear markers, limited spectral resolution of the acquisition device, calibration particularities, the subjectivity of the detection and quantification process, and inconsistencies between human operators of the analysis equipment. Embodiments of the present invention further provide an image processing technique which does not rely upon the subjective detection of contrast within the prepared sample or a complex and voluminous analysis of the sample at specific wavelengths of light using a combination of light sources and filters. Therefore, embodiments of the present invention provide a simpler and more effective colorimetric analysis technique that overcomes detection and quantification limitations in prior art analysis techniques, reduces subjectivity and inconsistency in the sample analysis, and is capable of providing the necessary analysis information about the sample, once an image of the sample is captured, without relying upon further examination of the sample to complete the analysis. These and other advantages are realized over prior art calorimetric analysis techniques as described herein.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
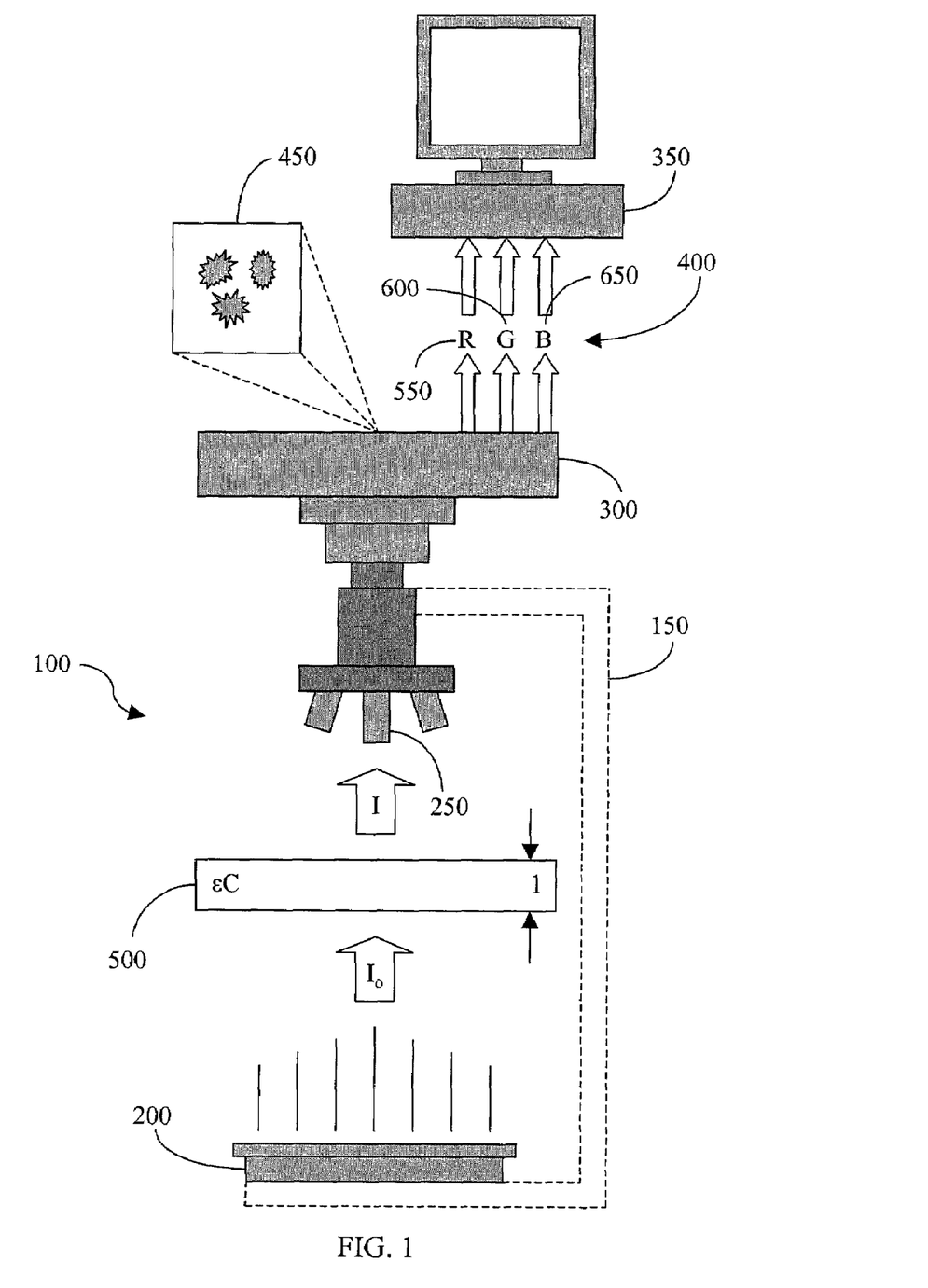
FIG. 1 is a general schematic representation of a quantitative video-microscopy system according to one embodiment of the present invention.

The platform for the evaluation of biological samples via image analysis is increasingly shifting from a general-purpose image analyzer to a more, and often highly, specialized dedicated "pathology workstation." Such workstations are typically designed to facilitate routine work, often combining many of the tools needed to provide a pathologist with the necessary information to determine the best possible results. One example of such a workstation is illustrated in FIG. 1 as a quantitative video-microscopy system, indicated by the numeral 100, according to one embodiment of the present invention. The system 100 generally comprises a microscope 150 having a light source 200 and a magnifying objective 250, a camera 300, a computer device 350, and a data transmission link 400 between the camera 300 and the computer device 350. The microscope 150 may comprise, for example, an Axioplan (or Axiovert) microscope produced by ZEISS of Germany or a similar microscope having a bright field light source. The camera 300 operably engages the microscope 150 and, in one embodiment, comprises a 3CCD RGB camera such as, for instance, a Model No. DC-330E Dage-MTI RGB 3CCD camera produced by Dage-MTI, Inc. of Michigan City, Ind. or a similar RGB camera. Typically, such a camera 300 also includes an associated frame grabber (not shown) to facilitate image capture, both the camera 300 and associated frame grabber being referred to herein as the "camera 300" for convenience. In some instances, both camera 300 and microscope 150 may be replaced by, for example, a linear flat scanner having a 3CCD chip or equivalent and a controlled illumination source. For instance, a Model No. Super CoolScan 4000 ED scanner produced by Nikon Corporation may be used for low-resolution imaging. Note that, though different configurations of the necessary system 100 are contemplated by the present invention, the present invention will be described herein in terms of a camera 300 and associated microscope 150. Accordingly, one skilled in the art will understand and appreciate the capabilities and methodologies associated with these different configurations for accomplishing the present invention as detailed herein.

The camera 300 is generally configured to capture an image 450 of a sample 500 through the magnifying objective 250 (where a flat scanner is used, the image 450 is captured through internal lenses), wherein the image 450 may further comprise a digital image having corresponding image data (collectively referred to herein as "the image 450"). The image 450 is generally captured as a whole, wherein the corresponding image data comprises a red channel 550, a green channel 600, and a blue channel 650 image of the field of view. The data transmission link 400 is configured so as to be capable of transmitting the image 450 to the computer device 350, wherein the computer device 350 is further configured to be capable of analyzing the image 450 with respect to each of the red 550, green 600, and blue 650 channels.

According to a particularly advantageous aspect of the present invention, the system 100 is configured to analyze the sample in accordance with the Lambert-Beer law. The Lambert-Beer law generally describes a proportionality that can be observed between the concentration of molecules in a solution (the concentration of the "molecular specie" or the "sample") and the light intensity measured through the solution. The Lambert-Beer law is typically expressed as:

$$OD = \epsilon \cdot l \cdot C \qquad (1)$$

where OD is the optical density of the solution, $\epsilon$ is a proportionality constant called the molar extinction or absorption coefficient, l is the thickness of the sample, and C is the concentration of the molecular specie. The absorption coefficient $\epsilon$ is specific to the molecular specie and is typically expressed in units of $L \cdot mol^{-1} \cdot cm^{-1}$.

This proportionality relationship defined by the Lambert-Beer law has been verified under the several conditions including, for example, monochromatic light illuminating the sample, low molecular concentration within the sample, generally no fluorescence or light response heterogeneity (negligible fluorescence and diffusion) of the sample, and lack of chemical photosensitivity of the sample. Further, another requirement for an analysis according to the Lambert-Beer law includes, for instance, correct Koehler illumination of the sample under the microscope. Koehler illumination is available with many modern microscopes, providing an even illumination of the sample in the image plane and allowing for effective contrast control. Koehler illumination is critical for certain processes such as, for example, densitometry analysis. Correct Koehler illumination is typically provided by, for example, a two-stage illuminating system for the microscope in which the source is imaged in the aperture of the sub-stage condenser by an auxiliary condenser. The sub-stage condenser, in turn, forms an image of the auxiliary condenser on the object. An iris diaphragm may also be placed at each condenser, wherein the first iris controls the area of the object to be illuminated, and the second iris varies the numerical aperture of the illuminating beam.

The Lambert-Beer law has an additive property such that, if the sample comprises several light-absorbing molecular species, for example, $s_1$ and $s_2$, having respective concentrations $C_1$ and $C_2$, the OD of a sample of thickness l (where $l_1=l_2=l$ for the sample, as indicated in the solution hereinafter) can be expressed as:

$$OD = \epsilon_1 \cdot l_1 \cdot C_1 + \epsilon_2 \cdot l_2 \cdot C_2 \qquad (2)$$

This situation may occur, for example, in a biological analysis where a "scene," a field of view, or a portion of the sample has been stained with two dyes consisting of a marker dye for targeting the molecular specie of interest and a counterstain for staining the remainder of the sample.

In order to accurately measure the concentration of given species imaged under a microscope, the measurements of the optical densities performed at different wavelengths must specifically correspond to the observed portion of the sample. That is, the microscopy system must be corrected for chromatic aberration, wherein such a correction or compensation may be accomplished by hardware, software, or a combination of software and hardware. Generally, glass tends to disperse light, which typically causes a simple glass lens to, for example, focus blue light at a shorter distance than red light. That is, a simple glass lens will exhibit different focal lengths for light comprising different wavelengths. This dispersion characteristic of glass gives rise to two observed effects. First, longitudinal chromatic aberration, or the positional difference of the focal points for different wavelengths of light along the vertical axis, is observed where, upon focusing the image for selected wavelengths of light corresponding to a particular color, the image will tend to be slightly out of focus when viewed under wavelengths of light corresponding to other colors. For example, in an RGB color space, if the image is focused for green wavelengths of light, the same image will tend to be out of focus when viewed under blue or red wavelengths of light. Secondly, lateral chromatic aberration is observed as a difference in magnification for light of different wavelengths due to the different focal lengths thereof. For example, in an RGB color space, an image viewed under relatively short blue light wavelengths will appear larger than the same image viewed under relatively longer red light wavelengths.

In microscopy systems having high quality objectives such as, for instance, apochromatic objectives, a large portion of the apparent chromatic aberration may be corrected. However, some residual lateral chromatic aberration may still remain, resulting in differences in magnification across wavelengths of light. This lateral chromatic aberration may be difficult to visually observe since a human observer tends to concentrate on the center of the field of view where the lateral aberration is typically absent. However, when imaging the field of view using, for example, a CCD camera, a very small lateral chromatic aberration resulting in, for instance, even less that 1% difference in magnification between wavelengths, will result in slight color shifts about the edges of objects in the field of view, but located away for the optical center of the objective. Consequently, a pixel located at a given (x,y) position on the image may not exactly depict the corresponding portion of the object under investigation depending on the wavelengths of light used to illuminate the object and the location of the object within the field of view. However, in order to solve chromagen separation equations derived from the Lambert-Beer law, a basic premise is that the exact same part of the object in the field of view must be examined. Therefore, images obtained for separate wavelengths of light must be adjusted to provide correlation with respect to the regions of the field of view where chromagen separation equations must be solved.

Accordingly, one advantageous aspect of the present invention involves a method of correcting lateral chromatic aberration within a microscopy system. First, the coordinates of the center of the magnifying objective 250 are determined with respect to the center of the electronic device or chip comprising the image-producing component of the camera 300. An observed magnification factor is then determined for each wavelength and compared to the magnification factor for an arbitrary chosen wavelength. For example, in an RGB color space, the central wavelength, namely the green channel 600 would comprise the chosen wavelength to which the magnification factor for each of the red 550 and blue 650 channels would be compared. The image for each wavelength is then adjusted according to the determined relative magnification factor and the relative coordinates of the center of the magnifying objective 250.

In order to facilitate the first two steps of the described method, a specific calibration slide is used, wherein the slide is configured with a grid of regularly spaced fine holes through a light blocking media. An image of the grid is taken at each wavelength of light used to illuminate the sample. For example, an image may be produced for each of the red 550, green 600, and blue 650 channels. The center of each hole is then computed in, for instance, x,y coordinates. The image corresponding to the wavelength of light nearest to the mean of the wavelengths of light under consideration (the green channel 600, for example) is then designated as the reference image. Subsequently, each of the images for the other wavelength under consideration is then compared to the reference image. For each hole in the grid, the difference in the x direction ($\delta x$) and the difference in the y direction ($\delta y$) are then determined for the corresponding hole in the reference image and the image being compared thereto. Equations such as, for example, linear equations that minimize the reconstruction error for $\delta x$ as a function of x and $\delta y$ as a function of y, are then determined. From these two equations, the center of the objective ($x_o, y_o$) is determined, where $x_o$ comprising the solution of the first equation in x when $\delta x$ is 0 and $y_o$ comprises the solution of the second equation in y when $\delta y$ is 0. A linear equation that minimizes the reconstruction error of $\delta d$, where $\delta d = (\delta x^2 + \delta y^2)^{1/2}$, as a function of the distance to the center of the objective is then determined, wherein the slope of that equation provides the magnification factor of the particular wavelength with respect to the reference wavelength. This image for the particular wavelength is then spatially adjusted such that the origin of the image corresponds to the center of the objective and the magnification of the image corresponds to the magnification of the reference image.

Once the microscope 150 has been configured to provide Keohler illumination for image acquisition and chromatic aberrations have been addressed, the additive property of the Lambert-Beer law can be applied to chromagen separation. For instance, the additive property of the Lambert-Beer law can be expanded to a situation in which the scene is analyzed in a color environment, generated by, for example, an RGB camera, separated into a red, green, and blue channel. In such an instance, the marker dye (or "dye 1") exhibits absorption coefficients, $\epsilon_{1r}, \epsilon_{1g}$, and $\epsilon_{1b}$, in the red, green and blue channels, respectively. Note that, in some instances, the analysis of the image in each of the red, green, and blue channels is equivalent to analyzing a red representation of the image across the red spectra, a green representation of the image across the green spectra, and a blue representation of the image across the blue spectra. Accordingly, the counterstain (or "dye 2") exhibits absorption coefficients, $\epsilon_{2r}$, $\epsilon_{2g}$, and $\epsilon_{2b}$, in the red, green and blue channels, respectively. Therefore, according to the additive property of the Lambert-Beer law, analysis of the sample in the RGB environment leads to three equations for the optical density thereof:

$$OD_r = \epsilon_{1r} \cdot l_1 \cdot C_1 + \epsilon_{2r} \cdot l_2 \cdot C_2 \quad (3)$$

$$OD_g = \epsilon_{1g} \cdot l_1 \cdot C_1 + \epsilon_{2g} \cdot l_2 \cdot C_2 \quad (4)$$

$$OD_b = \epsilon_{1b} \cdot l_1 \cdot C_1 + \epsilon_{2b} \cdot l_2 \cdot C_2 \quad (5)$$

where $OD_r$, $OD_g$, and $OD_b$ represent the optical densities of the sample measured in the red, green and blue channels, respectively. Still further, in the case of increased sample preparation complexity such as, for example, the treatment of the sample with three different dyes, equations (3), (4), and (5) become:

$$OD_r = \epsilon_{1r} \cdot l_1 \cdot C_1 + \epsilon_{2r} \cdot l_2 \cdot C_2 + \epsilon_{3r} \cdot l_3 \cdot C_3 \quad (6)$$

$$OD_g = \epsilon_{1g} \cdot l_1 \cdot C_1 + \epsilon_{2g} \cdot l_2 \cdot C_2 + \epsilon_{3g} \cdot l_3 \cdot C_3 \quad (7)$$

$$OD_b = \epsilon_{1b} \cdot l_1 \cdot C_1 + \epsilon_{2b} \cdot l_2 \cdot C_2 + \epsilon_{3b} \cdot l_3 \cdot C_3 \quad (8)$$

In such a situation, the three dyes may comprise, for instance, one marker dye and two counterstains, or two marker dyes and one counterstain, or even three separate marker dyes. It will be understood by one skilled in the art, however, that this demonstrated property of the Lambert-Beer law may be expanded to included an even greater plurality of dye combinations in accordance with the spirit and scope of the present invention. Note also that one particularly advantageous embodiment of the present invention utilizes a fast capture color imaging device such as, for example, a 3CCD RGB camera, for multi-spectral imaging of the markers over three distinct (red, green, and blue) channels. Accordingly, the exemplary analysis herein is presented in terms of three equations, though one skilled in the art will appreciate that the demonstrated concept may be applied to as many channels as are available with a particular imaging device.

In applying the Lambert-Beer law to a digital microscopy system 100 according to embodiments of the present invention, it is difficult and complex, inaccurate, or sometimes not possible to measure the thickness l of the sample 500. In such instances, the concentration C of the molecular specie can be extended and examined as the product of l and C (l·C) and the results treated accordingly. For example, where the concentration of one dye is being compared to the concentration of another dye in a particular sample, the sample thickness term will be common to both concentrations and thus it becomes less important to determine the sample thickness as an absolute and accurate value. Accordingly, it will be understood by one skilled in the art that an accurate determination of the thickness of the sample is typically not required, but may generally be treated as a constant in examining the equations as detailed herein.

The application of the Lambert-Beer law to a digital microscopy system 100 of the present invention also recognizes that the Lambert-Beer law can also be expressed as:

$$OD_{(x,y)} = \log I_{0(x,y)} - \log I_{(x,y)} \quad (9)$$

for a digital image 450 of the sample 500 comprising a plurality of pixels arranged, for example, according to a Cartesian coordinate system, where (x,y) signifies a particular pixel in the image 450, $OD_{(x,y)}$ is the optical density of the sample 500 at that pixel, $I_{(x,y)}$ is the measured light intensity or transmittance of the sample 500 at that pixel, and $I_{0(x,y)}$ is the light intensity of the light source 200 as measured without any intermediate light-absorbing object, such as the sample. Accordingly:

$$IOD = \sum_N (\log I_{0(x,y)} - \log I_{(x,y)}) \quad (10)$$

where IOD is the integrated optical density of the digital image 450 of the sample 500, and N is the number of pixels in the surface image 450 of the sample. It will further be appreciated by one skilled in the art that the logarithmic relationship described in equations (9) and (10) may be expressed in various bases within the spirit and scope of the present invention. For example, the relationships may be expressed in base 2, base 10, or natural logarithms, wherein the various bases are related by respective proportionality constants (for example, $\ln(x)$ or $\log_e(x) = 2.3026 \log_{10}(x)$). Thus, the proportionality constant may be appropriately considered where relative comparisons are drawn in light intensities. Further, in quantitative microscopy according to the Lambert-Beer law, the proportionality relationship between the optical density OD of the sample and the dye concentrations is conserved.

Therefore, for a prepared sample 500 examined by the system 100, the appropriate relation is expressed as:

$$\ln I_0 - \ln I = \ln I_0/I = OD = \epsilon \cdot l \cdot C \quad (11)$$

Where, for example, an 8 bit RGB camera 300 is used in the system 100, the light intensity transmitted through the sample in each channel may be expressed as $2^8$ (=256) values between 0 and 255. For example, the initial intensity $I_o$ of the light source 200, which corresponds to 100% transmittance, will preferably be expressed in each of the red 550, green 600, and blue 650 channels as a value approaching 255, representing the brightest possible value in each channel. The camera 300 and/or the light source 200 may be adjusted accordingly such that, in the absence of the sample, a pure "white" light will have an intensity value of 255 in each of the red 550, green 600, and blue 650 channels, corresponding to 100% transmittance. Conversely, in the absence of light, generally corresponding to transmittance approaching 0%, a "black image" will have an intensity value approaching 0 in each of the red 550, green 600, and blue 650 channels. At any pixel, the initial intensity $I_o$ of the light source 200, corresponding to 100% transmittance, is therefore expressed as the difference between the intensity value measured in presence of the light source 200 minus the intensity value measured in absence of the light source 200 for each of the red 550, green 600, and blue 650 channels. Because the intensity of the light source 200 may vary spatially across the image 450, or over the measured field of view, and because the magnifying objective 250 or other optical components may heterogeneously absorb light, 100% transmittance may be represented by various differential intensities over the measured field of view. However, since the optical density OD of the sample is expressed as the logarithm of the ratio of light transmittance in absence of the sample (initial intensity $I_o$) to light transmittance in presence of the sample (I), the optical density OD is largely spatially insensitive to small variations in the differential intensities over the measured field of view.

Since the light source 200 remains substantially constant over time, or can be easily re-evaluated, the measurement of the light intensity for any pixel, in the presence of the sample, can be translated into the transmittance I at that pixel and in each of the red 550, green 600, and blue 650 channels. Once values for the initial intensity $I_o$ and transmittance I are determined, the optical density OD can be computed. As such, at any location in the field of view 450 where a unique dye is present (as the only light-absorbing object between the light source 200 and the camera 300), the absorption coefficient $\epsilon$ of that dye may be determined in each of the red 550, green 600, and blue 650 channels. More particularly, l·C for a given pixel will be equal in each of the red 550, green 600, and blue 650 channels. Thus, if both l and C are known, the absorption coefficient $\epsilon$ can be computed according to equation (11) or in each of the red 550, green 600, and blue 650 channels as:

$$\epsilon_r = OD_r/(l \cdot C) = (\ln(I_{or}/I_r))/(l \cdot C) \quad (12)$$

$$\epsilon_g = OD_g/(l \cdot C) = (\ln(I_{og}/I_g))/(l \cdot C) \quad (13)$$

$$\epsilon_b = OD_b/(l \cdot C) = (\ln(I_{ob}/I_b))/(l \cdot C) \quad (14)$$

However, l·C is typically not known for a particular pixel in an image of a particular sample. Therefore, the absorption coefficients C are computed for each channel according to the ratio of the optical density OD in each channel, measured at a given pixel, to the maximum optical density OD out of all the channels measured at the same pixel. More particularly, it will be appreciated by one skilled in the art that the determination of the absorption coefficient $\epsilon$ in each of the red 550, green 600, and blue 650 channels, in the absence of a priori knowledge of l and/or C, is a matter of manipulating the linear equations in order to achieve a relative solution where l·C is arbitrarily set to a value of 1, wherein:

$$\epsilon_r = OD_r/1 = OD_r = \ln(I_{or}/I_r) \quad (15)$$

$$\epsilon_g = OD_g/1 = OD_g = \ln(I_{og}/I_g) \quad (16)$$

$$\epsilon_b = OD_b/1 = OD_b = \ln(I_{ob}/I_b) \quad (17)$$

Consequently, if the absolute concentration of the particular dye remains unknown, a relative absorption coefficient $\epsilon$, in each of the red 550, green 600, and blue 650 channels and for any given pixel, may be computed with an error factor equal to l·C.

Alternatively, because l is unique at a given pixel location and can be arbitrarily set to a value of 1, equations (6–8) may be rewritten as follow where $C_1$, $C_2$ and $C_3$ are related by a factor of l:

$$OD_r = \epsilon_{1r} \cdot C_1 + \epsilon_{2r} \cdot C_2 + \epsilon_{3r} \cdot C_3 \quad (18)$$

$$OD_g = \epsilon_{1g} \cdot C_1 + \epsilon_{2g} \cdot C_2 + \epsilon_{3g} \cdot C_3 \quad (19)$$

$$OD_b = \epsilon_{1b} \cdot C_1 + \epsilon_{2b} \cdot C_2 + \epsilon_{3b} \cdot C_3 \quad (20)$$

Note that the determination of an absorption coefficient $\epsilon$ matrix for different dyes may be performed independently of sample evaluation and stored for further application to samples treated with at least one of the respective dyes. Further, the various absorption coefficient $\epsilon$ matrices for particular dyes, as well as the original light intensity $I_o$ data for the light source 200 may be stored in, for example, the computer device 350, a server located on an intranet or the Internet, or other data storage device as will be appreciated by one skilled in the art. As such, when absorption coefficients $\epsilon$ have been evaluated for the different dyes, and optical densities OD have been determined from image data, the appropriate equations may be solved as a set of linear equations so as to extract the respective concentrations of the dyes $C_1$, $C_2$ and $C_3$.

By way of further explanation, a representative set of linear algebraic equations may be, for example, expressed as:

$$\begin{aligned} a_{11}x_1 + a_{12}x_2 + a_{13}x_3 + \ldots + a_{1N}x_N &= b_1 \\ a_{21}x_1 + a_{22}x_2 + a_{23}x_3 + \ldots + a_{2N}x_N &= b_2 \\ a_{31}x_1 + a_{32}x_2 + a_{33}x_3 + \ldots + a_{3N}x_N &= b_3 \\ \overline{a_{M1}x_1 + a_{M2}x_2 + a_{M3}x_3 + \ldots + a_{MN}x_N} &= b_M \end{aligned} \quad (21)$$

where, for N unknowns, $X_j$, j=1, 2, ..., N are related by M equations. The coefficients $a_{ij}$, where i=1, 2, ..., M and j=1, 2, ..., N, are generally known, as are the quantities $b_i$, i=1, 2, ..., M. If M<N, there are effectively fewer equations than unknowns. In such a case, there can be either no solution or more than one solution matrix x. Further, if N=M, then there are as many equations as unknowns and a unique solution matrix x may likely be determined. In addition, if M>N, then there are more equations than unknowns and, in general, no particular solution matrix x to the set of equations. Accordingly, the set of equations is said to be over-determined and, in such a case, the most appropriate solution is generally considered to be the solution providing the best fit for the equations, wherein the best fit solution typically corresponds to the solution having the minimal sum of reconstruction errors.

Equation (21) may also be alternatively expressed as:

$$A \cdot x = b \quad (22)$$

where "·" denotes matrix multiplication, A is the matrix of coefficients, and b is the right side portion expressed as a column vector. Generally, by convention, the first index of an element $a_{ij}$ denotes the element row; while the second index the element column. Further, $a_i$ or a[i] denotes an entire row a[i][j], j=1, ..., N. Accordingly, the solution of the matrix equation A·x=b for an unknown vector x, where A is the matrix of coefficients, and b is the right side portion, usually requires the determination of $A^{-1}$ or the matrix inverse of the matrix A. Thus:

$$x = A^{-1} \cdot b \quad (23)$$

Since $A^{-1}$ is the matrix inverse of matrix A, then $A \cdot A^{-1} = A^{-1} \cdot A = ID$, where ID is an identity matrix. To facilitate the determination of a solution, parameters may be established such that the number of equations is greater than or equal to the number of unknowns, or M≧N. As previously discussed, when M>N occurs there is, in general, no particular solution matrix x to equation (21) and the set of equations is over-determined. In such situations, however, the best "compromise" or best fit solution is often the solution that most closely and simultaneously satisfies all of the equations. Such closeness may be defined in, for example, a least-squares manner, wherein the sum of the squares of the differences between both sides of equation (21) is minimized. As a result, the over-determined set of linear equations may typically be reduced to a solvable linear problem, often referred to as a linear least-squares problem, that may be solved with singular value decomposition (SVD) mathematics as will be appreciated by one skilled in the art. SVD is directed to the parametric modeling of data and is usually the chosen method for solving linear least-squares problems and is described in further detail in, for example, NUMERICAL RECIPES IN C: THE ART OF SCIENTIFIC COMPUTING (ISBN 0-521-43108-5) Copyright (C) 1988–1992 by Cambridge University Press. Programs Copyright (C) 1988–1992 by Numerical Recipes Software.

In some situations, pre-computing solutions for all possible pixel values from the described system configuration may effectively facilitate real time processing of the image analysis. More particularly, if an 8 bit color image acquisition device such as, for example, an 8 bit 3CCD RGB camera is utilized, the measured light intensity I of a sample will have 256 possible values ranging between limits of 0 and 255 in each of the red 550, green 600, and blue 650 channels. In such an instance, all possible gray values ($256^3$ possible gray values for an 8 bit system) with respect to the original light intensity $I_o$ may be pre-computed and stored, for example, as a look-up table (LUT) within the computer device 350. Thus, for a sample 500 stained with a particular dye, the transmitted light intensity I (or the optical density OD) can be measured at a pixel in each of the red 550, green 600, and blue 650 channels and then compared to the previously stored gray values and the absorption coefficient $\epsilon$ matrix for that particular dye to thereby determine the dye concentration C, or an estimate thereof as the product l·C, at that pixel. Accordingly, an 8 bit system will provide 256(red channel)×256(green channel)×256(blue channel)=$256^3$ possible gray value solutions, thereby amounting to a 16 MB LUT for each dye. A system having a gray value resolution exceeding 8 bits per channel will lead to larger LUTs such as, for example, a LUT of>1GB for a system resolution of 10 bits per channel, wherein the computer device 350 may be appropriately configured to provide the necessary computing and/or storage capabilities.

The operation of the system 100 as described above may be further illustrated by example, assuming that the light source is a "white" light having $I_o$=255 in each of the red 550, green 600, and blue 650 channels and that three dyes are used having the following transmitted light intensity I characteristics in each of the red 550, green 600, and blue 650 channels:

| I | Red | Green | Blue |
|---|---|---|---|
| Dye 1 | 168 | 127 | 94 |
| Dye 2 | 94 | 241 | 247 |
| Dye 3 | 120 | 94 | 155 |

The corresponding optical density OD matrix (each element being computed as $\ln(I_o/I)$) thus becomes:

| OD | Red | Green | Blue |
|---|---|---|---|
| Dye 1 | 0.417 | 0.697 | 0.998 |
| Dye 2 | 0.998 | 0.056 | 0.032 |
| Dye 3 | 0.754 | 0.998 | 0.498 |

However, since OD=$\epsilon$·l·C, the OD values for each dye can be normalized with respect to the channel having the highest OD so as to provide a matrix of relative absorption coefficients $\epsilon$ for the respective dyes, since the l·C values will be constant across the channels. Accordingly:

| $\epsilon$ | Red | Green | Blue |
|---|---|---|---|
| Dye 1 | 0.418 | 0.698 | 1.000 |
| Dye 2 | 1.000 | 0.057 | 0.032 |
| Dye 3 | 0.755 | 1.000 | 0.499 |

Subsequently, assuming that a sample 500 has been stained with the same three dyes, Dye 1, Dye 2, and Dye 3, and that a light source 200 with similar spectral characteristics is used to illuminate the sample 500, an image 450 of the sample 500 is captured by the camera 300. At a particular pixel in the image 450, the computer device 350 then determines that the transmitted light intensity in each of the red 550, green 600, and blue 650 channels is:

| | Red | Green | Blue |
|---|---|---|---|
| I | 89 | 168 | 154 |
| where: | | | |
| $I_0$ | 255 | 255 | 255 |
| Thus: | | | |
| OD | 1.053 | 0.417 | 0.504 | for the particular pixel. Therefore, in order to determine the concentrations of the three dyes at that pixel, the OD matrix is multiplied by the inverse of the previously-determined relative absorption coefficient $\epsilon$ matrix ((OD)·$\epsilon^{-1}$=l·C). Accordingly:

| | l · C (mole · cm/L) or $C_{relative}$ |
|---|---|
| Dye 1 | 0.455 |
| Dye 2 | 0.829 |
| Dye 3 | 0.058 |

According to the methodology described herein, the determined gray levels or, in this example, RGB transmittance values from any combination of the three subject dyes may be used to reconstruct an artificial image, since there are no unknowns. Accordingly, for that particular pixel and the determined dye concentrations, images for single dyes would correspond to the following Black and White (BW) or RGB pixel intensities:

$$\ln(I_{BW})=\ln(I_o)-OD_{BW}, \text{ where } OD_{BW}=C \quad (24)$$

$$\ln(I_r)=\ln(I_o)-OD_r, \text{ where } OD_r=\epsilon_r\cdot C \quad (25)$$

$$\ln(I_g)=\ln(I_o)-OD_g, \text{ where } OD_g=\epsilon_g\cdot C \quad (26)$$

$$\ln(I_b)=\ln(I_o)-OD_b, \text{ where } OD_b=\epsilon_b\cdot C \quad (27)$$

Accordingly:

| | C | Intensity (I) | | | |
|---|---|---|---|---|---|
| Dye | Evaluated | BW | Red | Green | Blue |
| Dye1 | 0.455 | 161 | 210 | 185 | 161 |
| Dye2 | 0.829 | 111 | 111 | 243 | 248 |
| Dye3 | 0.058 | 240 | 244 | 240 | 247 |

Further advantageous aspects of the present invention are realized as a result of the dye separation techniques using color video imaging as previously described herein. For example, an artificial image of the field of view may be generated in an RGB color space or in gray levels as a substantially real time or live image, or as a still image, using combinations of the dyes comprising a marker and/or a counterstain used to prepare the sample. More particularly, an artificial image of the field of view may be produced which shows the sample as affected by all of the dyes, the sample as affected by one or more marker dyes, or the sample as affected by the counterstain. Consequently, since the dyes used to prepare the sample are characterized by the system, the capabilities of the system may be extended such that, for instance, the sample or field of view may be automatically scanned to detect a specific region of interest as identified by the characteristics of a particular dye or to affect or facilitate a task to be performed on that specific region of interest.

According to one embodiment of the present invention, the system may be configured so as to be capable of detecting one or more particular dyes which have been previously characterized by the system. In some instances, such a dye may comprise, for example, the ink from a particular pen or similar ink marker that has been characterized by the system as having unique color features, these unique color features being retained by the system as a corresponding set of extinction coefficients. It follows that the system may be configured to recognize and respond to portions of the field of view in which this dye is identified and that, in some instances, the one or more particular markers may comprise a tangible portion of such a system as described herein. For instance, such a pen may be used, for example, where an operator such a pathologist or a cytotechnologist identifies special areas of interest on a sample-containing glass or plastic slide. A special area of interest may comprise, for example, a potential diagnostic area or a reference area. The operator, using the pen, may then surround the area with a line of ink from that pen. After processing a number of slides, the operator may feed the slides into, for instance, an automatic scanning system for quantitative evaluation. Having been configured to detect the ink from the pen, the system may then inclusively identify the area of interest, corresponding to the area within the ink line, circled by the operator with the pen. The system may thereafter appropriately process that area of the slide where, for example, one color of pen ink may indicate that a particular diagnostic evaluation must be performed, while another color of ink may indicate that the area contains a calibration or reference material and would call for the system to run a corresponding calibration procedure. Note that, in addition to slides, the described technique may be readily adapted to examine other mounting forms for microscopic material such as, for example, microtiter plates or microarrays. Thus, it will be appreciated by one skilled in the art that the capabilities of such embodiments of the system, configured to recognize particular dyes or inks, may extend to many different automatic scanning processes where interactive marking of areas of interest with specific pens, the pens having different color inks previously evaluated by the system, may be used to automatically designate and actuate a subsequent evaluation or other processing of that area of interest by an appropriate component of the system or other specified device.

Additionally, the artificial images of the field of view may also facilitate the presentation of the data in a configuration allowing identification and selection of meaningful objects or areas of interest as, for example, still images in a report prepared for diagnostic or other reporting purposes.

Other advantageous aspects of the present invention may also be realized from the described system and method herein. For instance, the differences in characteristics between the marker dyes and the counterstain, as realized in various dye-specific images of the sample, may be used to evaluate the focus adequacy of the field of view. More particularly, for example, the sample may be treated with two separate dyes, one dye comprising a nuclei stain and the other dye comprising a membrane stain. In such an instance, an image directed to the membrane stain may be evaluated for focus adequacy by examining the focus of the same image directed to the nuclei stain, wherein the nuclei stain image exhibits a more definite structure upon which evaluate focus.

Still further, the artificial image of the field of view may also be used to facilitate the identification and extraction of selected features of the treated sample. For example, marked point processes, contextual analysis, and/or geo-statistics may be used to identify and extract features from the image based on, for instance, a spatial distribution analysis of a particular dye. Such a feature extraction capability would also allow, for example, fields of view or objects of interest to be sorted, flagged, or otherwise identified or grouped based on, for instance, the overall content of a given marker dye or a selected ratio of particular marker. Where, for example, a threshold criteria can be established, such a capability would be the detection of rare, worsening, or other serious events. Proceeding further, classifiers based specifically on the image processing resulting from the counterstain and/or marker dye specific images may then be established and used to evaluate the presence of certain cell types or to perform a diagnosis based upon the field of view. For example, HER2 may be evaluated in this manner by comparison to a continuous diagnosis scale established according to the system and methods described herein. Such classifiers may usually also encompass other informative features such as, for example, detail based upon the morphology or the texture of the cells.

Still further, another advantageous aspect of the present invention is realized where the system is capable of processing the image data at a faster rate than the images are acquired. The enhanced speed at which the image data is processed may allow, for example, features indicated by a particular marker dye to be processed and classified. Accordingly, various conditions may be identified based upon predetermined criteria. As such, visual and/or sonic alarms may be established and/or mapped in conjunction with the processing of the image data. Thus, in some instances, the operator's attention may be directed to a specific field of view or object of interest when a characteristic of a marker attains a predetermined level in, for example, intensity or presence in a particular field.

Figure 2:
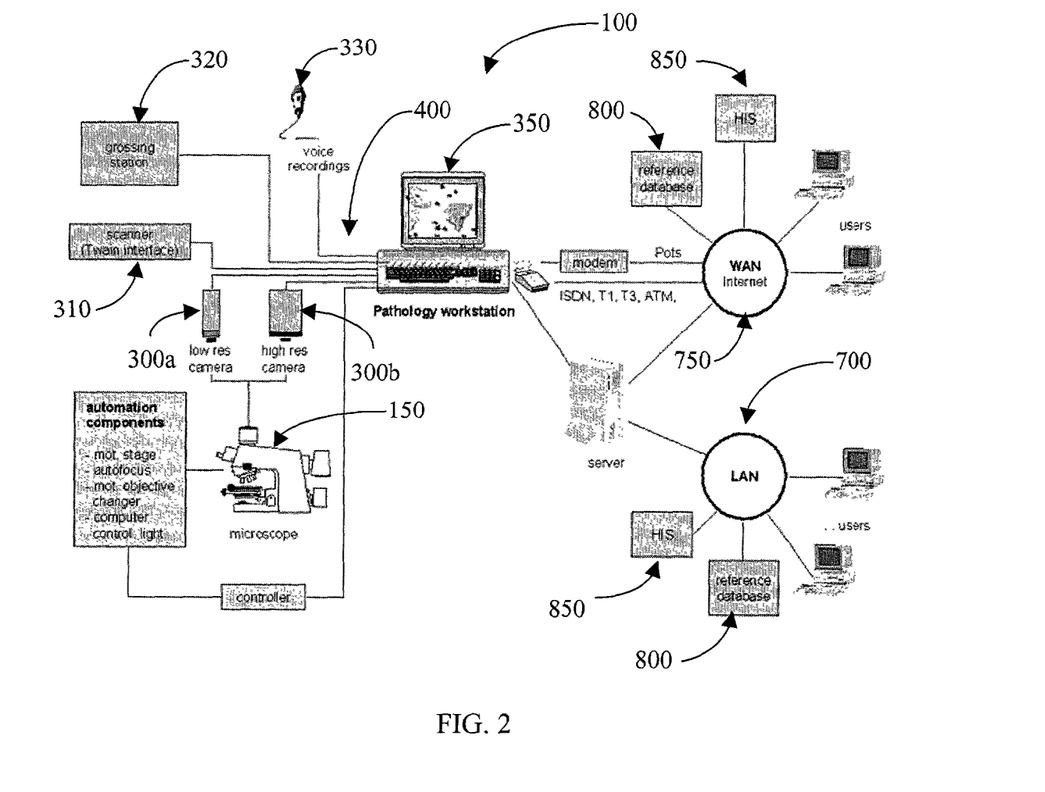
FIG. 2 is a schematic representation of the practical realization in an extended configuration of a quantitative video-microscopy system according to one embodiment of the present invention.

FIG. 2 is a schematic representation of a practical realization of an extended system configuration according to one embodiment of the present invention. In such an implementation, the system 100 or workstation is centered about a microscope 150. The microscope 150 may include one or more robotic components including, for example, a motorized stage, an automatic focus mechanism, a motorized objective changer, and an automatic light intensity adjustment. The system 100 may also include various input devices such as, for instances, cameras 300a and 300b having fast automatic focusing and configured for acquiring low-resolution and high-resolution images, a flat bed linear scanners 310 used for acquiring low-resolution images, a grossing station 320, and a voice-recording device 330, which are all linked to a computer device 350 through various data transmission links 400. The workstation 100 can be part of a Local Area Network (LAN) 700, but may also be configured to support different communication protocols such that available communication channels such as, for example, a standard telephone line, an ISDN connection, or a T1 line, can readily connect the workstation 100 to other components or devices over large distances via a Wide Area Network (WAN) 750 as will be appreciated by one skilled in the art.

If the pathology workstation 100 is configured to operate in an integrated environment, the WAN 700 or LAN 750 connection may permit access to, for instance, existing reference databases 800 and Hospital Information Systems (HIS) 850. With such a configuration, new samples and/or cases may readily be compared with the pictures and accompanying information of previously-accumulated reference cases. Further, images acquired from the samples and/or slides being examined at the workstation 100 can be complemented with the patient and case history as necessary.

In the extended configuration embodiment as shown in FIG. 2, the pathology workstation 100 is particularly configured for a comprehensive sample evaluation. For example, with information and digital pictures of the initial gross biological sample, images of the slides prepared from the sample can be prepared and processed as described herein. The patient and case information, the images, and the resulting quantitative information about the cell components of the sample and the sample architecture (in the case of, for instance, tissue samples) can collected, integrated if necessary, and stored in a single database. If, for example, an initial or second expert opinion is needed or if the slide is used for training or proficiency testing, the communication capabilities of the extended configuration along with the automation features of the microscope 150 may allow the workstation 100 to be used as a tele-pathology system. For example, high-resolution images directed to features or objects of interest characterizing a questionable situation on a particular slide may be electronically forwarded to the expert and/or to the audited candidate. In some instances, an overview picture of the slide may be provided, wherein the automated microscope 150 is used to scan the slide automatically on, for example, a field by field basis. The corresponding digital images may then be stored in the memory of the computer device 350. Where a field by field basis is used, the edges of adjacent fields may be precisely matched using correlation algorithms, so as to provide a single large overview image of the entire slide. Such an overview image may assist the reference pathologist in making an assessment of the information. In some instances, the reference pathologist may remotely control the workstation 100 from a remote site to acquire necessary and/or supplemental images which may be required so as to provide a correct and thorough assessment of the slide.

Subsequently, the information accumulated by the workstation 100 for a studied case such as, for instance, real or mathematically generated images, measurement results and graphical representations thereof, patient data, preparation data, and screening maps, may be selectively integrated into a report which can either be printed or accessed electronically. Such a report would provide a comprehensive picture of the case under evaluation and would also facilitate quality assurance and standardization issues.

It will be understood that the methodology and procedures detailed herein in conjunction with the system 100 specify a method of quantifying an amount of a molecular specie from an image of a sample captured by an RGB camera in a video-microscopy system. One skilled in the art will also appreciate that such a method may be automated so as to provide a computer software program product, executable on a computer device, having executable portions capable of quantifying the amount of a molecular specie from a digital image of a sample captured by a color image acquisition device, such as an RGB camera, in a video-microscopy system. Accordingly, embodiments of the system 100 describe the implementation of the method and/or the corresponding computer software program product which may be accomplished in appropriately configured hardware, software, or a combination of hardware and software in accordance with the spirit and scope of the present invention.

Thus, embodiments of the present invention comprise a colorimetric analysis technique for prepared samples that provides effective detection and quantification of species of interest that overcomes limiting factors of prior art techniques such as, for example, spectral overlapping, mixing of colors due to spatial overlap of membrane and nuclear markers, limited spectral resolution of the acquisition device, calibration particularities, the subjectivity of the detection and quantification process, and inconsistencies between human operators of the analysis equipment. Embodiments of the present invention further provide an image processing technique which does not rely upon the subjective detection of contrast within the prepared sample or a complex and voluminous analysis of the sample at specific wavelengths of light using a combination of light sources and filters. Therefore, embodiments of the present invention provide a simpler and more effective colorimetric analysis technique that overcomes detection and quantification limitations in prior art analysis techniques, reduces subjectivity and inconsistency in the sample analysis, and is capable of providing the necessary analysis information about the sample, once an image of the sample is captured, without relying upon further examination of the sample to complete the analysis.

More particularly and as demonstrated, the analysis (detection and quantification of a molecular specie of interest) of the prepared sample is accomplished through the measurement of light intensities that are manifested in a digital image of the sample captured by a color image acquisition device. Since the analysis is relatively image-dependent, rather than sample-dependent, redundant images may be captured for analysis, while many samples may be processed so as to capture the necessary images within a relatively short period of time. Once the image data has been captured and stored, the actual analysis may occur at a later time or as needed without requiring the physical presence of the actual sample. Such an analysis may be further applied to examining the entire sample or even the entire slide. Thus, embodiments of the present invention provide an expeditious quantitative video-microscopy system that permits the use of such a system as a routine or "production" tool capable of accomplishing a relatively high analysis throughput. As such, significant advantages are realized by embodiments of the present invention as compared to prior art quantitative microscopy systems which were typically limited in sample throughput and analysis, thus generally making such systems more useful as research tools.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed That which is claimed:

1. A method of determining an amount of at least one molecular specie comprising a sample, each molecular specie being indicated by a dye, said method comprising:
   determining an optical density of the sample from the image data, corresponding to an image of the sample captured by a color image acquisition device in a video-microscopy system, in each of a red, green, and blue channel and for a pixel in the image, so as to form a corresponding optical density matrix for the pixel;
   determining a relative absorption coefficient for the dye indicating each molecular specie, independently of the sample and in each of the red, green, and blue channels, so as to form a corresponding relative absorption coefficient matrix; and
   multiplying the optical density matrix by an inverse of the relative absorption coefficient matrix so as to form a resultant matrix for the pixel, the resultant matrix comprising the amount of each molecular specie, as indicated by the respective dye, for the pixel.

2. A method according to claim 1 wherein determining the relative absorption coefficient further comprises determining an initial intensity of a light emitted by a light source in each of the red, green, and blue channels.

3. A method according to claim 2 wherein determining the relative absorption coefficient further comprises illuminating each dye with the light source, independently of the sample, and determining a transmitted intensity of the light transmitted therethrough in each of the red, green, and blue channels.

4. A method according to claim 3 wherein determining the relative absorption coefficient further comprises comparing the initial intensity of the light to the transmitted intensity of light so as to determine an optical density for each dye in each of the red, green, and blue channels.

5. A method according to claim 3 wherein determining the relative absorption coefficient further comprises determining an optical density for each dye by determining a natural logarithm of a ratio of the initial intensity of the light to the transmitted intensity of the light in each of the red, green, and blue channels.

6. A method according to claim 5 wherein determining the relative absorption coefficient further comprises normalizing the optical density in each of the red, green, and blue channels, with respect to the channel having the highest optical density, for each dye.

7. A method according to claim 2 wherein determining an optical density of the sample further comprises illuminating the sample with the light source and determining a transmitted intensity of the light transmitted therethrough in each of the red) green, and blue channels.

8. A method according to claim 7 wherein determining an optical density of the sample further comprises comparing the initial intensity of the light to the transmitted intensity of the light so as to determine an optical density for the sample in each of the red, green, and blue channels.

9. A method according to claim 7 wherein determining an optical density of the sample further comprises determining a natural logarithm of the ratio of the initial intensity of the light to the transmitted intensity of the light through the sample in each of the red, green, and blue channels.

10. A method according to claim 1 further comprising capturing an image of the sample as image data in each of the red, green, and blue channels of at least one of an RGB camera and an RGB-configured scanner.

11. A method according to claim 1 further comprising illuminating the sample under Koehler illumination conditions.

12. A method according to claim 1 further comprising correcting chromatic aberration in the video-microscopy system.

13. A method of determining the amount of each of a plurality of molecular species comprising a sample, each molecular specie being indicated by a dye, at least one dye comprising a marker dye and another dye comprising a counterstain, said method comprising:
   determining an optical density of the sample from the image data, corresponding to an image of the sample captured by a color camera in a video-microscopy system, in each of a red, green, and blue channel and for a pixel in the image, so as to form a corresponding optical density matrix for the pixel;
   determining a relative absorption coefficient for at least the marker dye and the counterstain, independently of the sample and in each of the red, green, and blue channels, so as to form a corresponding relative absorption coefficient matrix; and
   multiplying the optical density matrix by an inverse of the relative absorption coefficient matrix so as to form a resultant matrix for the pixel, the resultant matrix comprising the amount of each molecular specie, as indicated by the respective dye, for the pixel.

14. A method according to claim 13 wherein determining the relative absorption coefficient further comprises determining an initial intensity of a light emitted by a light source in each of the red, green, and blue channels.

15. A method according to claim 14 wherein determining the relative absorption coefficient further comprises illuminating each dye with the light source, independently of the sample, and measuring a transmitted intensity of the light transmitted therethrough in each of the red, green, and blue channels.

16. A method according to claim 15 wherein determining the relative absorption coefficient further comprises comparing the initial intensity of the light to the transmitted intensity of light so as to determine an optical density for each dye in each of the red, green, and blue channels.

17. A method according to claim 15 wherein determining the relative absorption coefficient further comprises determining the optical density for each dye by determining a natural logarithm of a ratio of the initial intensity of the light to the transmitted intensity of the light in each of the red, green, and blue channels.

18. A method according to claim 17 wherein determining the relative absorption coefficient further comprises normalizing the optical density in each of the red, green, and blue channels, with respect to the channel having the highest optical density, for each dye.

19. A method according to claim 14 wherein measuring an optical density of the sample further comprises illuminating the sample with the light source and measuring a transmitted intensity of the light transmitted therethrough in each of the red, green, and blue channels.

20. A method according to claim 19 wherein measuring an optical density of the sample further comprises comparing the initial intensity of the light to the transmitted intensity of the light so as to determine an optical density for the sample in each of the red, green, and blue channels.

21. A method according to claim 19 wherein measuring an optical density of the sample further comprises calculating a natural logarithm of the ratio of the initial intensity of the light to the transmitted intensity of the light through the sample in each of the red, green, and blue channels.

22. A method according to claim 13 further comprising illuminating the sample under Koehler illumination conditions.

23. A method according to claim 13 further comprising correcting chromatic aberration in the video-microscopy system.

24. A video-microscopy system for determining an amount of at least one molecular specie comprising a sample, each molecular specie being indicated by a dye, from an image of the sample, said system comprising:
   a color image acquisition device configured so as to be capable of capturing a magnified digital image of the sample as image data;
   a computer device operably engaged with the image acquisition device and comprising:
      a processing portion configured to determine an optical density of the sample from the image data, in each of a red, green, and blue channel and for a pixel in the image, so as to form a corresponding optical density matrix for the pixel;
      a processing portion configured to determine a relative absorption coefficient for the dye indicating each molecular specie. independently of the sample and in each of the red, green, and blue channels, so as to form a corresponding relative absorption coefficient matrix; and
      a processing portion configured to multiply the optical density matrix by an inverse of the relative absorption coefficient matrix so as to form a resultant matrix for the pixel, the resultant matrix comprising the amount of each molecular specie, as indicated by the respective dye, for the pixel.

25. A system according to claim 24 wherein the image acquisition device comprises at least one of a scanner and a microscope operably engaged with a color camera.

26. A system according to claim 24 further comprising a light source directed toward the image acquisition device and configured to emit a light having an initial intensity in each of the red, green, and blue channels.

27. A system according to claim 26 wherein the light source is configured to illuminate the sample and the processing portion for determining optical density is further configured to direct a measurement of a transmitted intensity of the light transmitted through the sample in each of the red, green, and blue channels.

28. A system according to claim 27 wherein the processing portion for determining optical density is further configured to compare the initial intensity of the light to the transmitted intensity of the light so as to determine an optical density for the sample in each of the red, green, and blue channels.

29. A system according to claim 27 wherein the processing portion for determining optical density is further configured to calculate a natural logarithm of a ratio of the initial intensity of the light to the transmitted intensity of the light so as to determine am optical density for the sample in each of the red, green, and blue channels.

30. A system according to claim 26 wherein the computer device further comprises a processing portion configured to direct the light source to illuminate each dye, independently of the sample, and to direct a measurement of a transmitted intensity of the light transmitted therethrough in each of the red, green, and blue channels.

31. A system according to claim 30 wherein the computer device further comprises a processing portion configured to compare the initial intensity of the light to the transmitted intensity of the light so as to determine an optical density for each dye in each of the red, green, and blue channels.

32. A system according to claim 30 wherein the computer device further comprises a processing portion configured to determine the optical density for each dye by determining a natural logarithm of a ratio of the initial intensity of the light to the transmitted intensity of the light in each of the red, green, and blue channels.

33. A system according to claim 32 wherein the computer device further comprises a processing portion configured to normalize the optical density in each of the red, green, and blue channels, with respect to the channel having the highest optical density, for each dye so as to determine the respective relative absorption coefficient in each of the red, green, and blue channels.

34. A system according to claim 24 wherein the computer device further comprises a storage media configured to store the relative absorption coefficient in each of the red, green, and blue channels for a plurality of dyes, and wherein the dyes indicating the molecular species in the sample are selected from the plurality of dyes.

35. A system according to claim 34 wherein the computer device further comprises a processing portion configured to retrieve the respective relative absorption coefficients for each dye from the storage media, and to form the corresponding relative absorption coefficient matrix, in accordance with the dyes indicating the molecular species in the sample which are selected from the plurality of dyes.

36. A system according to claim 24 wherein the computer device further comprises a processing portion configured to invert the relative absorption coefficient matrix.

37. A system according to claim 26 wherein the light source is further configured to provide Koehler illumination conditions.

38. A system according to claim 24 wherein the image acquisition device is further configured to correct chromatic aberration.

39. A computer-readable medium encoded with a computer program capable of determining an amount of at least one molecular specie comprising a sample, each molecular specie being indicated by a dye, said computer-readable medium encoded with a computer program being executable on a computer device and comprising:
   an executable portion capable of determining an optical density of the sample from the image data, corresponding to a digital image of the sample captured by a color image acquisition device in a video-microscopy system, in each of a red, green, and blue channel and for a pixel in the digital image, so as to form a corresponding optical density matrix for the pixel;
   an executable portion capable of determining a relative absorption coefficient for the dye indicating each molecular specie, independently of the sample and in each of the red, green, and blue channels, so as to form a corresponding relative absorption coefficient matrix; and
   an executable portion capable of multiplying the optical density matrix by an inverse of the relative absorption coefficient matrix so as to form a resultant matrix for the pixel, the resultant matrix comprising the amount of each molecular specie, as indicated by the respective dye, for the pixel.

40. A computer-readable medium encoded with a computer program according to claim 39 further comprising an executable portion capable of directing a light source to illuminate the sample with a light having an initial intensity in each of the red, green, and blue channels.

41. A computer-readable medium encoded with a computer program according to claim 40 further comprising an executable portion capable of directing a measurement of a transmitted intensity of the light transmitted through the sample in each of the red, green, and blue channels.

42. A computer-readable medium encoded with a computer program according to claim 41 wherein the executable portion for determining an optical density is further capable of comparing the initial intensity of the light to the transmitted intensity of the light so as to determine an optical density for the sample in each of the red, green, and blue channels.

43. A computer-readable medium encoded with a computer program according to claim 41 wherein the executable portion for determining an optical density is further capable of calculating a natural logarithm of a ratio of the initial intensity of the light to the transmitted intensity of the tight so as to determine an optical density for the sample in each of the red, green, and blue channels.

44. A computer-readable medium encoded with a computer program according to claim 40 further comprising an executable portion capable of directing the light source to illuminate each dye, independently of the sample, and directing a measurement of a transmitted intensity of the light transmitted therethrough in each of the red, green, and blue channels.

45. A computer-readable medium encoded with a computer program according to claim 44 further comprising an executable portion capable of comparing the initial intensity of the light to the transmitted intensity of the light so as to determine an optical density for each dye in each of the red, green, and blue channels.

46. A computer-readable medium encoded with a computer program according to claim 44 further comprising all executable portion capable of determining the optical density for each dye by determining a natural logarithm of a ratio of the initial intensity of the light to the transmitted intensity of the light in each of the red, green, and blue channels.

47. A computer-readable medium encoded with a computer program according to claim 46 further comprising an executable portion capable of normalizing the optical density in each of the red, green, and blue channels, with respect to the channel having the highest optical density, for each dye so as to determine the respective relative absorption coefficient in each of the red, green, and blue channels.

48. A computer-readable medium encoded with a computer program according to claim 39 further comprising an executable portion capable of directing a storage media to store the relative absorption coefficient in each of the red, green, and blue channels for a plurality of dyes, and wherein the dyes indicating she molecular species in the sample are selected from the plurality of dyes.

49. A computer-readable medium encoded with a computer program according to claim 48 further comprising an executable portion capable of retrieving the respective relative absorption coefficients for each of the marker dye and the counterstain from the storage media, and forming the corresponding relative absorption coefficient matrix, in accordance with the dyes indicating the molecular species in the sample which are selected from the plurality of dyes.

50. A computer-readable medium encoded with a computer program according to claim 39 further comprising an executable portion capable of inverting the relative absorption coefficient matrix.

51. A computer-readable medium encoded with a computer program according to claim 40 wherein the executable portion capable of directing a light source is further configured to direct the light source to provide Koehler illumination conditions.

52. A computer-readable medium encoded with a computer program according to claim 39 further comprising an executable portion capable of directing the image acquisition device to correct chromatic aberration.

53. A method of determining an amount of at least one molecular specie comprising a sample, each molecular specie being indicated by a dye, said method comprising:
determining an optical density of the sample, from an image of the sample captured by an RGB camera in a video-microscopy system, in each of a red, green, and blue channel of the RGR camera and for a pixel in the image, so as to form a corresponding optical density matrix for the pixel;
determining a relative absorption coefficient for the dye indicating each molecular specie, independently of the sample and in each of the red, green, and blue channels, so as to form a corresponding relative absorption coefficient matrix; and
multiplying the optical density matrix by an inverse of the relative absorption coefficient matrix so as to form a resultant matrix for the pixel, the resultant matrix comprising the amount of each molecular specie, as indicated by the respective dye, for the pixel.

54. A method according to claim 53 wherein determining the relative absorption coefficient further comprised determining an initial intensity of a light emitted by a light source in each of the red, green, and blue channels of the RGB camera.

55. A method according to claim 54 wherein determining the relative absorption coefficient further comprises illuminating each dye with the light source, independently of the sample, and measuring a transmitted intensity of the light transmitted therethrough in each of the red, green, and blue channels of the RGB camera.

56. A method according to claim 54 wherein determining the relative absorption coefficient further comprises determining the optical density for each dye by determining a natural logarithm of a ratio of the initial intensity of the light to the transmitted intensity of the light in each of the red, green, and blue channels.

57. A method according to claim 56 wherein determining the relative absorption coefficient further comprises normalizing the optical density in each of the red, green, and blue channels, with respect to the channel having the highest optical density, for each dye.

58. A method according to claim 54 wherein measuring an optical density of the sample further comprises illuminating the sample with the light source and measuring a transmitted intensity of the light transmitted therethrough in each of the red, green, and blue channels of the RGB camera.

59. A method according to claim 58 wherein measuring an optical density of the sample further comprises comparing the initial intensity of the light to the transmitted intensity of the light so as to determine an optical density for the sample in each of the red, green, and blue channels.

60. A method according to claim 58 wherein measuring an optical density of the sample further comprises calculating a natural logarithm of the ratio of the initial intensity of the light to the transmitted intensity of the light through the sample in each of the red, green, and blue channels.

61. A video-microscopy system for determining an amount of at least one molecular specie comprising a sample, each molecular specie being indicated by a dye, from an image of the sample, said system comprising:
a microscope configured to form a magnified image of the sample;
an RGB camera having a red channel, a green channel, and a blue channel, and operably engaged with tho microscope so as to he capable of forming a digital image from the magnified image;
a Computer device operably engaged with the RGB camera and comprising:
a processing portion configured to determine an optical density of the sample in each of the red, green, and blue channels and for a pixel in the digital image so as to form a corresponding optical density matrix for the pixel;
a processing portion configured to determine a relative absorption coefficient for The dye indicating each molecular specie, independently of the sample and in each or the red, green, and blue channels, so as to form a corresponding relative absorption coefficient matrix; and
a processing portion configured to multiply the optical density matrix by an inverse of the relative absorption coefficient matrix so as to form a resultant matrix for the pixel of the digital image, the resultant matrix comprising tho amount of each molecular specie, as indicated by the respective dye, for the pixel.

62. A system according to claim 61 further comprising a light source directed toward the RGB camera and configured to emit a light having an initial intensity in each of the red, green, and blue channels.

63. A system according to claim 62 wherein the light source is configured to illuminate the sample with the light and the processing portion for determining an optical density is further configured to determine a transmitted intensity of the light transmitted through the sample in each of the red, green, and blue channels of the RGB camera.

64. A system according to claim 63 wherein the processing portion for determining an optical density is further configured to determine a natural logarithm of a ratio of the initial intensity of the light to the transmitted intensity of the light so as to determine an optical density for the sample in each or the red, green, and blue channels.

65. A system according to claim 62 wherein the computer device further comprises a processing portion configured to direct the light source to illuminate each dye with the light source, independently of the sample, and to direct a determination of a transmitted intensity of the light transmitted therethrough in each of the red, green, and blue channels of the RGB camera.

66. A system according to claim 65 wherein the computer device further comprises a processing portion configured to compare the initial intensity of the light to the transmitted intensity of the light so as to determine an optical density for each dye in each of the red, green, and blue channels.

67. A system according to claim 65 wherein the computer device further comprises a processing portion configured to determine an optical density for each dye by determining a natural logarithm of a ratio of the initial intensity of the light to the transmitted intensity of the light in each of the red, green, and blue channels.

68. A system according to claim 67 wherein the computer device further comprises a processing portion configured to normalize the optical density in each of the red, green, and blue channels, with respect to the channel having the highest optical density, for each dye so as to determine the relative absorption coefficient in each of the red, green, and blue channels.

69. A system according to claim 61 wherein the computer device further comprises a storage media configured to store the relative absorption coefficient in each of the red, green, and blue channels for a plurality of dyes, and wherein the dyes indicating the molecular species in the sample are selected from the plurality of dyes.

70. A system according to claim 69 wherein the computer device further comprises a processing portion configured to retrieve the respective relative absorption coefficients for each dye from the storage media, and to form the corresponding relative absorption coefficient matrix, in accordance with the dyes indicating the molecular species in the sample which are selected from, the plurality of dyes.

71. A system according to claim 61 wherein the computer device further comprises a processing portion configured to invert the relative absorption coefficient matrix.

72. A system according to claim 62 wherein the light source is further configured to provide Koehler illumination conditions.

73. A system according to claim 61 wherein at least one of the microscope, the RGB camera, and the computer device is further configured to correct chromatic aberration.

74. A computer-readable medium, encoded with a computer program capable of determining an amount of at least one molecular specie comprising a sample, each molecular specie being indicated by a dye, said computer-readable medium encoded with a computer program being configured to be executed on a computer device and comprising:
an executable portion capable of determining an optical density of the sample, from a digital image of the sample captured by an RGB camera in a video-microscopy system, in each of the red, green, and blue channels of the RGB camera and for a pixel in the digital images so as to form a corresponding optical density matrix for the pixel;
an executable portion capable of determining a relative absorption coefficient for the dye indicating each molecular specie, independently of the sample and in each of the red, green, and blue channels, so as to form a corresponding relative absorption coefficient matrix; and
an executable portion capable of multiplying the optical density matrix by an inverse of the relative absorption coefficient matrix so as to form a resultant matrix for the pixel of the digital image, the resultant matrix comprising the amount of each molecular specie, as indicated by the respective dye, for the pixel.

75. A computer-readable medium encoded with a computer program according to claim 74 further comprising an executable portion capable of directing a light source to illuminate the sample with a light having an initial intensity in each of the red, green, and blue channels.

76. A computer-readable medium encoded with a computer program according to claim 75 further comprising an executable portion capable of determining a transmitted intensity of the light transmitted through the sample in each of the red, green, and blue channels of the RGB camera.

77. A computer-readable medium encoded with a computer program according to claim 76 wherein the executable portion for determining an optical density is further capable of comparing the initial intensity of the light to the transmitted intensity of the light so as to determine an optical density for the sample in each of the red, green, and blue channels of the RGB camera.

78. A computer-readable medium encoded with a computer program according to claim 76 wherein the executable portion for determining an optical density is further capable of calculating a natural logarithm of a ratio of the initial intensity of the light to the transmitted intensity of the light so as to determine an optical density for the sample in each of the red, green, and blue channels of the RGB camera.

79. A computer-readable medium encoded with a computer promgram according to claim 75 further comprising an executable portion capable of directing the light source to illuminate each dye, independently of the sample, and directing a determination of a transmitted intensity of the light transmitted therethrough in each of the red, green, and blue channels of the RGB camera.

80. A computer-readable medium encoded with a computer program according to claim 79 further comprising an executable portion capable of comparing the initial intensity of the light to the transmitted intensity of light so as to determine an optical density for each dye in each of the red, green, and blue channels.

81. A computer-readable medium encoded with a computer program according to claim 79 further comprising an executable portion capable of determining an optical density for each dye by determining a natural logarithm of a ratio of the initial intensity of the light to the transmitted intensity of the light in each of the red, green, and blue channels.

82. A computer-readable medium encoded with a computer program according to claim 81 further comprising an executable portion capable of normalizing the optical density in each of the red, green, and blue channels, with respect to the channel having the highest optical density, for each dye so as to determine the relative absorption coefficient in each of the red, green, and blue channels.

83. A computer-readable medium encoded with a computer program according to claim 74 further comprising an executable potion capable of directing a storage media to store the relative absorption coefficient in each of the red, green, and blue channels for a plurality of dyes, and wherein the dyes indicating the molecular species in the sample are selected from the plurality of dyes.

84. A computer-readable medium encoded with a computer program according to claim 83 further comprising an executable portion capable of retrieving the respective relative absorption coefficients for each dye from the storage media, and forming the corresponding relative absorption coefficient matrix, in accordance with the dyes indicating the molecular species in the sample which are selected from the plurality of dyes.

85. A computer-readable medium encoded with a computer program according to claim 74 further comprising an executable portion capable of inverting the relative absorption coefficient matrix.

86. A computer-readable medium encoded with a computer program according to claim 75 wherein the executable portion capable of directing a light source is further configured to direct the light source to provide Koehler illumination conditions.

87. A computer-readable medium encoded with a computer program according to claim 74 further comprising an executable portion capable of directing the RGB camera to correct chromatic aberration.

* * * * *

UNITED STATES PATENT AND TRADEMARK OFFICE
CERTIFICATE OF CORRECTION

PATENT NO. : 7,065,236 B2
APPLICATION NO. : 09/957446
DATED : June 20, 2006
INVENTOR(S) : Marcelpoil et al.

It is certified that error appears in the above-identified patent and that said Letters Patent is hereby corrected as shown below:

Column 21,
Line 57, ")" should read --,--.

Column 23,
Line 62, "am" should read --an--.

Column 27,
Line 10, "tho" should read --the--;
Line 11, "he" should read --be--;
Line 21, "The" should read --the--;
Line 23, "or" should read --of--;
Line 30, "tho" should read --the--.

Column 30,
Line 6, "potion" should read --portion--.

Signed and Sealed this

Twenty-sixth Day of December, 2006

JON W. DUDAS
*Director of the United States Patent and Trademark Office*